(12) United States Patent
Tai

(10) Patent No.: US 6,740,890 B1
(45) Date of Patent: May 25, 2004

(54) TIME-RESOLVED LIGHT DECAY MEASUREMENTS WITHOUT USING A GATED DETECTOR

(76) Inventor: Chen-Yu Tai, 3326 Christie Blvd., Toledo, OH (US) 43606

( * ) Notice: Subject to any disclaimer, the term of this patent is extended or adjusted under 35 U.S.C. 154(b) by 140 days.

(21) Appl. No.: 09/931,214

(22) Filed: Aug. 15, 2001

(51) Int. Cl.[7] .............................................. G01N 21/64
(52) U.S. Cl. ................................ 250/458.1; 250/459.1; 356/317; 356/417
(58) Field of Search .......................... 250/458.1, 459.1, 250/461.1; 356/317, 318, 417

(56) References Cited

U.S. PATENT DOCUMENTS

| | | | | |
|---|---|---|---|---|
| 4,855,930 A | * | 8/1989 | Chao et al. ................... | 702/32 |
| 5,323,010 A | * | 6/1994 | Gratton et al. ........... | 250/458.1 |
| 6,071,748 A | * | 6/2000 | Modlin et al. .............. | 436/174 |
| 6,377,346 B1 | * | 4/2002 | Vaisala et al. .............. | 356/417 |
| 6,455,861 B1 | * | 9/2002 | Hoyt ....................... | 250/458.1 |
| 6,483,582 B2 | * | 11/2002 | Modlin et al. .............. | 356/317 |
| 2002/0020818 A1 | * | 2/2002 | Mitchell et al. ......... | 250/459.1 |

* cited by examiner

*Primary Examiner*—Albert Gagliardi
(74) *Attorney, Agent, or Firm*—Marger Johnson & McCollom, PC

(57) ABSTRACT

The present invention relates to the measurement of the time dependence of light emitted by a material after it is excited by a light or electric pulse. An embodiment of this invention utilizes a CCD camera and a mask with slits for time resolved spectroscopy of fluorescent materials illuminated with a light pulse. By converting a slit in space to a gate in time, the whole decay curve of the fluorescence may be obtained with a single material-exciting light pulse. The systems and methods of the present invention are particularly suitable for DNA and protein study.

34 Claims, 7 Drawing Sheets

AT t=10⁻ μs

AT t=10⁺ μs

AT t=20⁻ μs

AT t=20⁺ μs

AT t=30⁻ μs

AT t=30⁺ μs

TIME-RESOLVED LIGHT DECAY MEASUREMENTS WITHOUT USING A GATED DETECTOR

BACKGROUND OF THE INVENTION

The present invention relates generally to light detectors and more particularly to a system for measuring the decay time constant of light emitted from a molecule after it is excited by a pulse of light or electric current.

Luminometry is a highly sensitive detection technique to detect the presence or concentration of a specific material, such as bio-medical molecules. However, the luminescent molecules can be very sensitive to environment variations, and most substances emit light that contributes to an unpredictable background luminance. Time-resolved spectroscopy is attractive because a molecule is identified by its specific decay constant that is not sensitive to the environment condition. With background luminance quickly reduced, the delayed fluorescence technology is a contrast enhancing mechanism.

The conventional time-resolved spectroscopic detection system requires a short pulsed light, or electric source and a "gated" detector. In a typical time resolved fluorescence microscopy, a gated detector is synchronized, with controllable delay time, to the excitation of the specimen by a laser, a flush lamp, or a pulsed LED (light emitting diode). An intensified CCD (charge-coupled device) camera can be easily gated for time resolved fluorescence study. Use of the intensified CCD camera, however, causes a deteriorating signal to noise ratio, because the thermal noise from the photocathode as well as electron multiplication noise from the microchannel plate reduces the signal to noise ratio. In addition, image intensifiers cause a reduction in the intra-scene dynamic range.

Other gating technologies have their drawbacks. A gated photomultiple tube may also be used as a gated detector. However, the signal is read point by point with this method. A rotating wheel with holes is another gating technology used in time-resolved spectroscopy. Application of this slow gating technology is limited to molecules with a very long decay lifetime. With conventional "gating" technology, such as intensified CCD, the signal is observed only at the "gated time interval" for each exciting pulse. Most of the fluorescent light that falls outside the time gate is wasted.

Other time-resolved fluorescence detection methods include modulating the exciting light and deriving the decay time constant from the phase shift of the modulated signal relative to the exciting light, or deriving the decay time constant by studying the polarization measurement. Each of these methods has drawbacks that are well known by practitioners in the art.

The main difficulty in time-resolved fluorescence spectroscopy is therefore developing a suitable light measurement technology for luminance decay detection over time. Accordingly, the need remains for overcoming problems inherent with time resolved fluorescence spectroscopy and to develop a suitable time-resolved light detection system.

SUMMARY OF THE INVENTION

The present invention relates to a technology that is based on the conversion of a slit in space to a gate in time to perform time resolved spectroscopy.

In an embodiment of this invention, the measurement system of the present invention utilizes a CCD (charge coupled device) camera to measure the intensity of the light emitted from a sample. The CCD camera has rows and column of pixels. Charge stored in the pixels can be transferred in parallel rows. In a preferred implementation of the invention, the CCD pixels are covered with a mask that has slits. When the sample under study is illuminated with a short light pulse and fluoresces, an image of the sample forms on the mask. With the mask blocking most of the area, only pixels underneath the slit are exposed to the fluorescent light. When charges in the pixels are transferred in parallel in a certain direction at a constant rate, the whole decay curve of the fluorescence can be detected with a single exciting light pulse.

The proposed technology will therefore have the advantage in efficiency over existing technologies. More importantly, with the whole decay curve recorded with each single pulse, "noises" caused by fluctuation in the power of an individual exciting light pulse, which happens in all of the gated detection system, is eliminated.

The invention will become more readily apparent from the following Detailed Description, which proceeds with reference to the drawings, in which:

DETAILED DESCRIPTION OF THE INVENTION

Figure 1A:
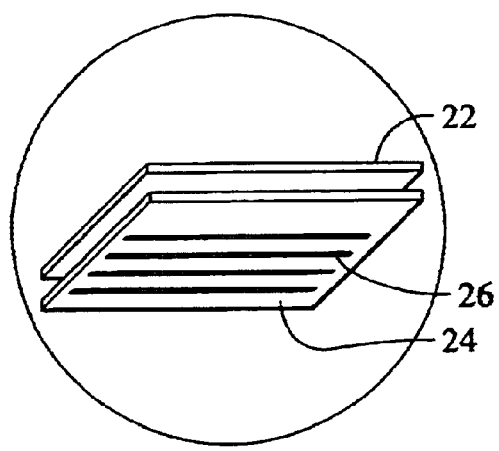
FIGS. 1 and 1A are schematic diagrams of a time-resolved fluorescence detection system without a gating device constructed according to a preferred embodiment of the invention.
Figure 1:
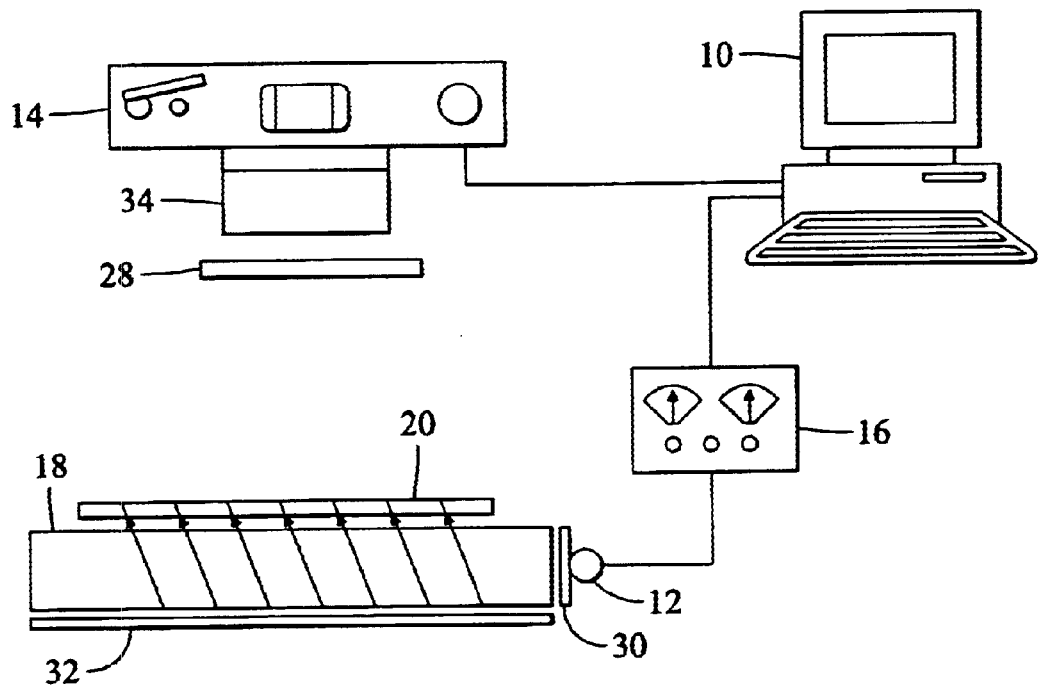

Referring now to drawings, wherein like components are designated by the like reference numerals throughout the various figures, attention is directed to FIG. 1 which shows a time-resolved fluorescent detecting system that uses no time gate device. In this system, a computer 10 is used to control the data recording and handling processes. A set of LEDs 12 provides the exciting light, and a CCD (charge coupled device) camera 14 is the fluorescent light detector.

To start the process of time resolved spectroscopic study of the sample, an electric signal is sent from the computer 10 to trigger a pulsed power supply 16 which turns on the LEDs 12. The lighting system in this particular example also include a light guide 18, which expand light beam output from the point light sources, the LEDs 12, to a plane light source. The beam expanding technology is already discussed in applicants' U.S. Pat. Nos. 5,506,929, 5,668,913, 5,835,661 and 5,854,872 and is thus not described in detail here. The object of the measurement, a sample of material 20 that emits fluorescent light when it is illuminated with the exciting light, is placed above the light guide 18 to intercept the pulsed light.

In the insert shown at FIG. 1A, the CCD 22 in the CCD camera 14 is covered with a mask 24. The mask is made of a material that is opaque to the fluorescent light and has slits 26 that transmits fluorescent light. A filter 28 is placed between the CCD 14 and the sample 20 to cut down the background luminance. This filter 28 will block the exciting light, e.g. light emitted by the LEDs 14, but transmits fluorescent light emitted by the sample 20. A short pass filter 30 is placed between the light source 12 and the sample to further reduce the background luminance. The short pass filter transmits light with the correct wavelength for excitation, but blocks long wavelength light. A lens 34 in the CC!) camera 14 projects the image of the sample on the CCD 22. A reflector 32 is placed underneath the light guide 18 to enhance the brightness.

In order to demonstrate the principle of operation of this invention, we will make a brief description of the CCD. A charge-coupled device (CCD) is an ultra-sensitive light detector made of silicon or similar material. The silicon film can easily absorb photons of light that are incident on its surface. When a photon is absorbed, a single electron is released that is free to move around in the silicon crystal lattice structure. CCDs are specially designed to "store" these generated electrons and prevent them from wandering around the lattice. In this way a pattern of electrons is built up in the CCD that directly corresponds to the pattern of the photons of light received. The CCD chip basically consists of a thin slice of silicon substrate covered by a two-dimensional array of polysilicon electrodes that are separated by oxide insulation layers.

Figure 2:
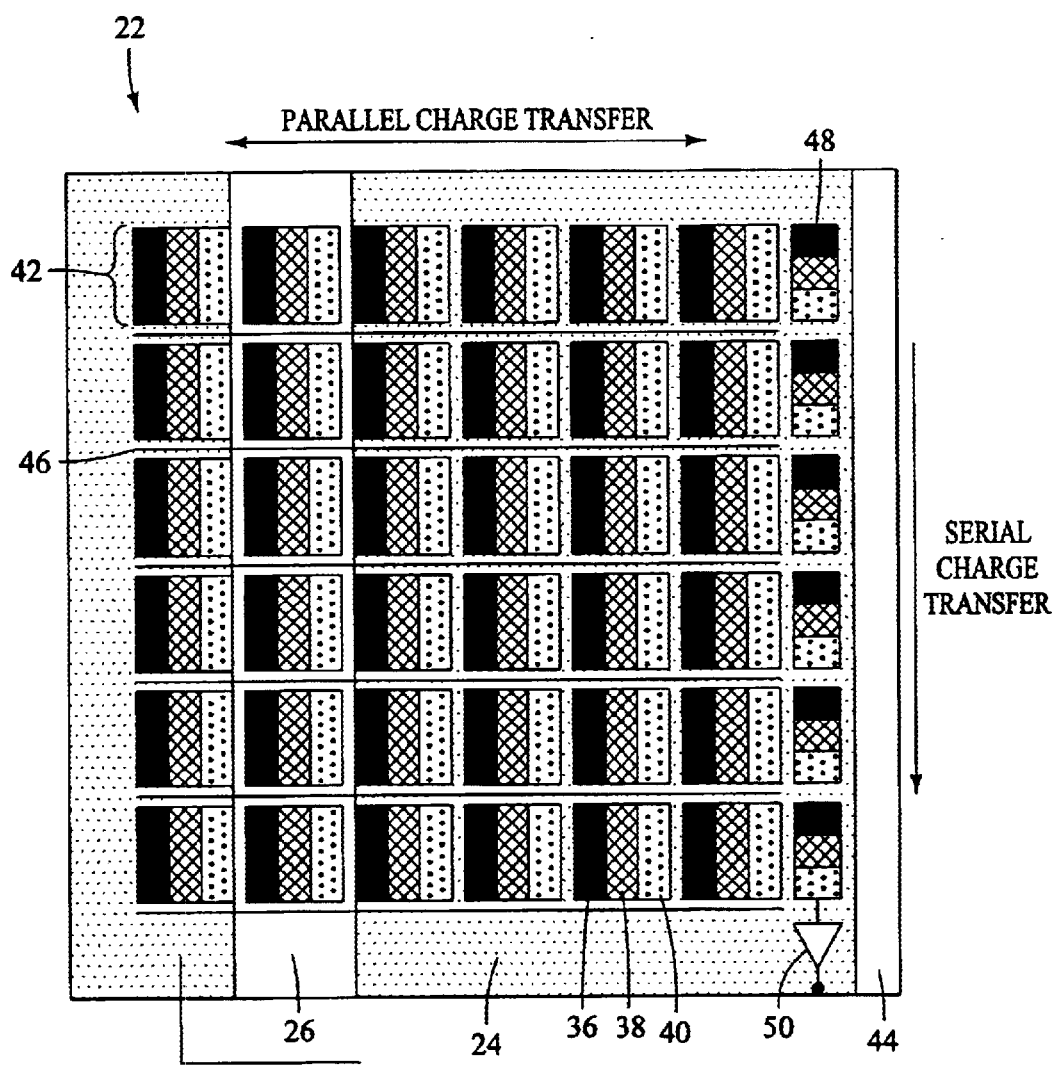
FIG. 2 is a schematic diagram of a three phase CCD covered with a mask that has slits.

Many of the CCDs are known as three-phase CCDs. The layout of a "small", 6 row by 6 column, three-phase CCD, together with the mask, is shown in FIG. 2. In this type of CCD, the silicon is covered with three sets of electrode strips 36, 38, 40. A pixel 42, which is composed of a set of three electrodes is isolated from the silicon substrate 44 and from other pixels. One of the three electrodes 38 is biased more positively than the other two, and it is under this one that the electrons generated by the incident light are accumulated. The electrons are restrained from moving along the length of the electrode (up-down in FIG. 2; left-right in FIGS. 3A–3F) by "Channel Stops" 46, which are narrow regions of heavily doped material. Their negative charge repels electrons and therefore prevents movement across the stop 46. At any time, the charge accumulated under one electrode on the CCD can be transferred to the area below an adjacent electrode if the adjacent electrode potential is raised while the first is lowered. The parallel charge transfer and the serial charge transfer direction are shown in FIG. 2. The transfer of charge may be in either direction depending only on the order in which the electrode voltage are raised or lowered. All the charges stored over the entire two-dimensional imaging area are moved simultaneously in the relevant direction in a parallel charge transfer. This process may be repeated in order to transfer the accumulated two-dimensional charge over many pixels. Once the charge from one row (exposed under slit 26) is in the serial output register 48, it may be transferred to an "Output Amplifier" 50, located at one end of the serial output register. The charge in the output register is transferred one at a time to the output. In this way the charge pattern, corresponding to the intensity of incident photons of light, can be moved along the CCD.

The minimum line transfer time can be as short as 0.3 microseconds ($\mu$s). Here it should be noted that some CCDs incorporate a charge transfer channel, termed "interline mask", or use a light tight mask to cover one half of the parallel array as a storage area, to achieve rapid charge transfer. With this approach, the signal is being integrated on the light sensitive portion of the sensor while the stored charge is read out.

Now we will describe the proposed technology to perform time resolved spectroscopy without using a gated detector. Turning now again to FIG. 1, for simplicity, we assume the "shuttle" of the CCD camera is "open" (alternately, the CCD camera has no shuttle), and all of the pixels are "cleared" when a command to start the data recording procedure is given by the computer 10. To demonstrate this technology, we assume that the driving pulse to light the LEDs 12 has a duration of 5 $\mu$s. For the purpose of demonstration, we will assume the CCD 22 has 400×400 pixels. We further assume that it takes less than 1.0 $\mu$s to accomplish the process of transferring charges by one line in parallel charge transfer.

To demonstrate the proposed technology, we also assume that the sample 20 is a "gel" with "DNA bands". In this arrangement, the CCD 22 is covered with a mask 24 that has four slits 26. Each slit 26 on the mask 24 covering the CCD 22 exposes only one column of the CCD pixels, as demonstrated in FIG. 2. The CCD camera 14 is arranged in such a way that the center of the image of the "bands" falls on the slits 26. In this example, there will be ninety-nine columns of un-illuminated pixels between the lighted rows of pixels.

The grid of pixels illustrated in FIG. 2 is shown rotated ninety degrees in FIGS. 3A–3F so that columns in FIG. 2 become "rows" in FIGS. 3A–3F.

Figure 3A:
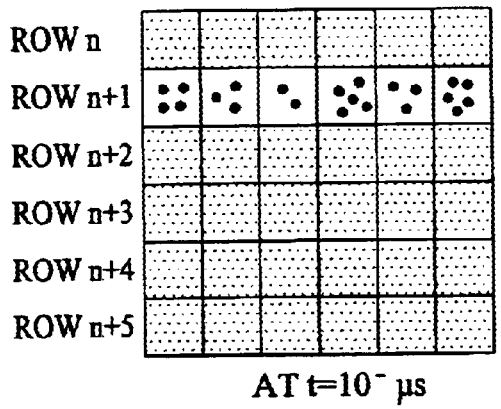
FIG. 3A shows charge distribution of pixels in the FIG. 2 CCD at $10.0^{-}\mu s$ in the example.
Figure 3B:
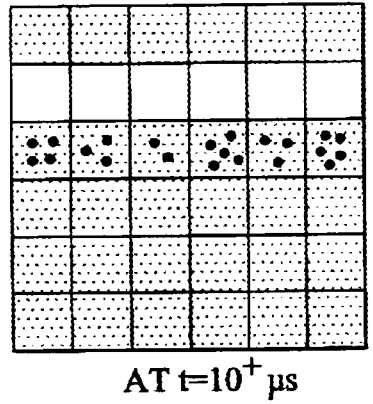
FIG. 3B shows charge distribution of pixels in the FIG. 2 CCD at $10.0^{+}\mu s$ in the example.
Figure 3C:
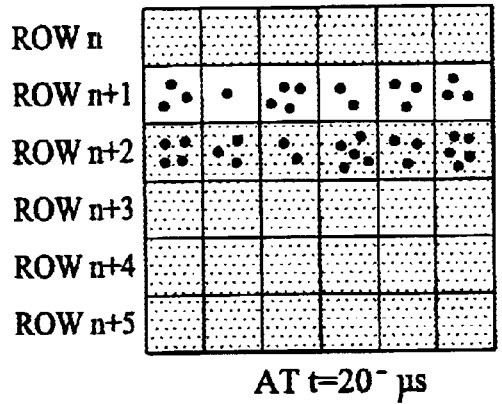
FIG. 3C shows charge distribution of pixels in the FIG. 2 CCD at $20.0^{-}\mu s$ in the example.
Figure 3D:
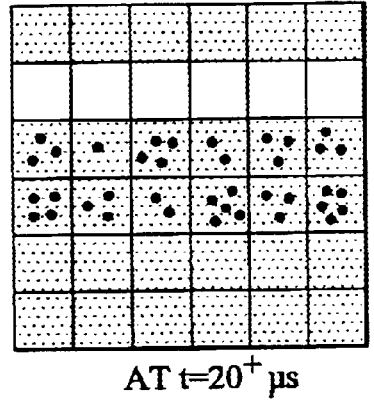
FIG. 3D shows charge distribution of pixels in the FIG. 2 CCD at $20.0^{+}\mu s$ in the example.
Figure 3E:
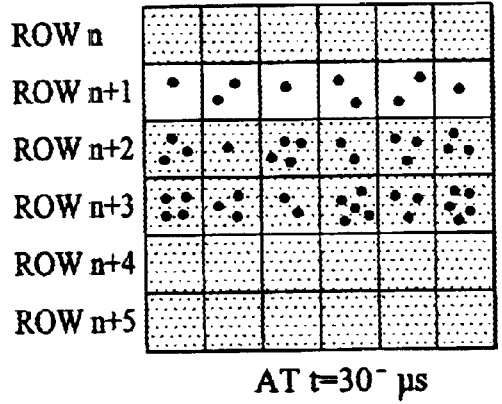
FIG. 3E shows charge distribution of pixels in the FIG. 2 CCD at $30.0^{-}\mu s$ in the example.
Figure 3F:
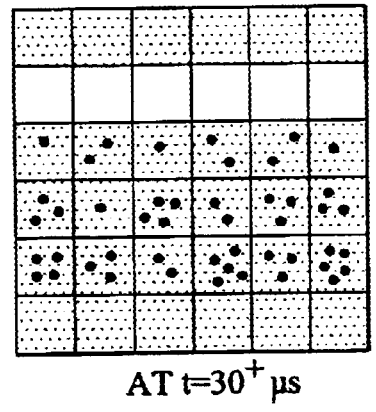
FIG. 3F shows charge distribution of pixels in the FIG. 2 CCD at $30.0^{+}\mu s$ in the example.

Let us designate the column exposed beneath a certain slit 26 as "Row n+1". As described above, the exciting light (from LEDs) is turned on at t=0. At the same time (t=0), a command is given by the computer 10 to the CCD camera 14 to make a parallel charge transfer by one line in the normal direction (towards the serial output register) every 10 $\mu$s. Assuming the transfer is made exactly at t=10.0 $\mu$s, then at time t=10.0$^-\mu$s (slightly less than 10.0 $\mu$s), the charge in row n to row n+5 may have the distribution shown in FIG. 3A. Similarly, at t=10.0$^+\mu$s (slightly over 10,0 $\mu$s), the parallel charge transfer process has been accomplished and the charge will now have a distribution shown in FIG. 3B. Row n+2 will now have the charge accumulated for a time period of 10.0 $\mu$s at t=0. Similarly, row n+1 will now have no charge left at all. At t=20.0$^-\mu$s, row n+1 will now have charge accumulated in the slit area for 10.0 $\mu$s, as shown in FIG. 3C. The parallel charge transfer process continues and at t=20.0$^+\mu$s the second parallel charge transferring process will be accomplished. FIG. 3D shows charge distribution at t=20.0$^+\mu$s. Now, rows n+2, and n+3 will each have the charge accumulated over the slit area for a time period of 10.0 $\mu$s, starting from t=10.0 $\mu$s, and t=0.0 $\mu$s, respectively. FIG. 3E shows the charge distribution in the six rows (columns in FIG. 2) at t=30.0 $\mu$s and FIG. 3F shows the charge distribution at t=30.0$^+\mu$s. Each pixel in rows n+2, n+3 and n+4 now holds charges accumulated over a time period of 10.0 μs, starting at t=20.0 μs, t=10.0μs and t=0, respectively.

The charge transfer process will continue for a predetermined time. To further demonstrate the proposed approach, let us assume that the process proceeds 10 times. That is, at t=100.0$^+$μs, the computer will stop the command for charge transfer. At t=100.0$^+$μs, row n+2 to row n+1 will each have charges accumulated over a time period of 10.0 μs, with accumulation time starting varies from t=90.0 μs, to t=0. Charges stored in row n+2 to row n+1, therefore, provide information on the time dependence of the fluorescent signal for a duration of 10.0 μs. This approach can therefore provide the whole decay curve of the fluorescent light after the sample is irradiated with a single light pulse.

Figure 4:
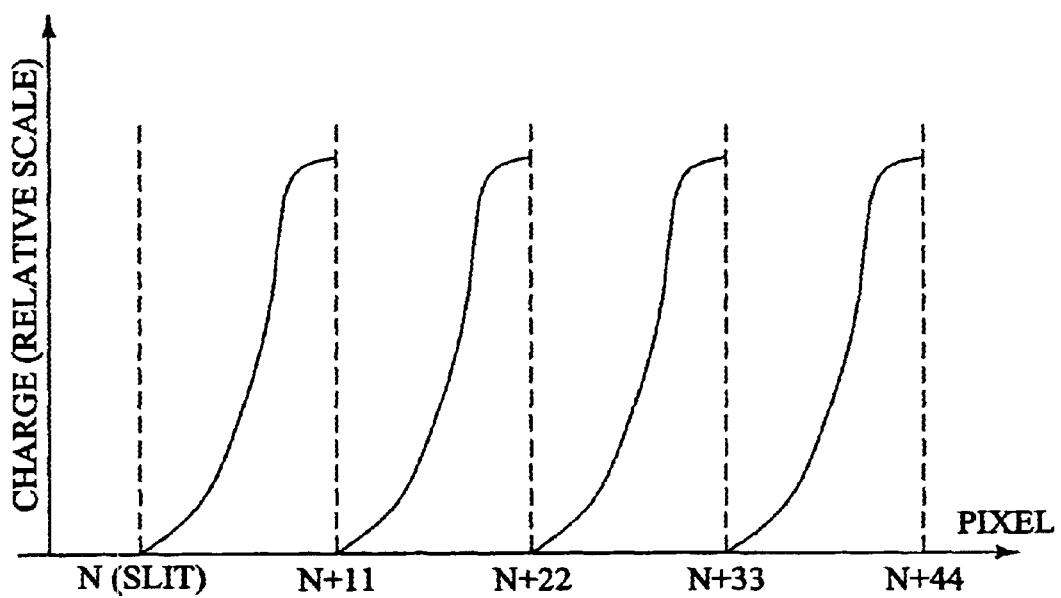
FIG. 4 illustrates charge distribution in the pixels at $t=3110.0\ \mu s$ in the example.

Now, we have described the principle of time resolved spectroscopy with no gated detector. Data acquisition with a single excitation light pulse with this technology is described. To improve the signal to noise ratio, an efficient data integration method is desirable. With the straightforward method, it is inefficient to store data accumulated in a computer data file and then integrate the data pulse by pulse. This is because the read out process is very slow, because the charge in each pixel is read one pixel at a time. Here, we will present an efficient data integration method, which is also based on parallel charge transfer in CCD 22. In the example described above, there are 99 rows of pixels between two adjacent slits and only 10 of these rows have charges. To demonstrate the data integration approach, let us assume that the fluorescent light decays with a decay constant of approximately 50.0 μs. At t=1,000.0 μs, the fluorescent light will be reduced to approximately $2 \times 10^{-9}$ of its maximum value. With our data integration method, the computer 10 will give an instruction to the CCD 22 to make one more parallel charge transfer at t=1,000.0 μs. After this charge transfer is accomplished, the computer 10 will give a command to turn on the LED 12 again, and to start the process of charge transfer ten more times, exactly as the process described above, after the first excitation light pulse is turned on. At t=1110.0 μs, charges stored in row n+13 to row n+22 of the CCD 22 will provide information on the time dependence of the fluorescent signal for the first light pulse, and charges stored in row n+2 to row n+11 will provide information on the time dependence of the fluorescent signal for the second light pulse. Row n+12 stores charge resulting from accumulated incident light through slit 26 over time period t=100.0$^+$μs and t=1,000.0 μs, and serves as a buffer between row set n+2 to n+1 and n+13 to n+22. This process may proceed nine times to record time resolved fluorescence for nine light pulses, for a total time duration of 9110.0 μs. Charge distribution in the pixels at t=3110.0 μs is shown in FIG. 4.

If it is desired to integrate data for more than nine times, one may send a command to the CCD camera 14 at t=10 ms to transfer data in the BACKWARD DIRECTION by 100 lines. This process will be accomplished in 100.0 μs. At time t=1.1 ms, a command will again be given by the computer to turn on the LED 12 and to repeat the data integration process, as described above. At t=19.11 ms, data stored on each row of pixels will be corresponding to a time resolved fluorescence signal integrated over two light pulses. Fluorescent decay signal for a total of eighteen light pulses will therefore be recorded. This process may continue until a predetermined number of pulse excitation and data integration processes are accomplished. The data may then be transferred, one by one, to the computer data file for data analysis.

In the above embodiment, the width of the slit, the rate of charge transfer, the number of pixels in the CCD 22, and the distance between the slits, are all provided only for demonstration. The invention is not limited to any of the assumed numbers.

In the detection system described above, a mask 24 with a physically cut slit 26 is placed in front of the CCD 22. The type of mask has a fixed number of slits, each located at a predetermined location. DNA bands in the gel have to be located in such a location that its image falls on the slits to be recorded. This system is therefore not flexible for many applications.

In the second embodiment of this invention, a programmable mask is presented to overcome the shortcomings. A particular "programmable mask" proposed in this invention is essentially a black and white "LCD" (liquid crystal display) panel. The liquid crystal panel has "pixels" that can be turned "on" or "off". The pixels are transparent when they are in the "on" state, and opaque when they are in the "off" state. Since the "on/off" turning speed of the LCD is not a concern for this application, a simple low cost STN type, black and white, LCD is suitable for this application. With the LCD panel connected through a "driver card" to the computer, one can program the location, width, and length of the "slits". With the "programmable mask", one can even "scan" the slits to achieve the time resolved spectrum of the whole area.

Figure 5:
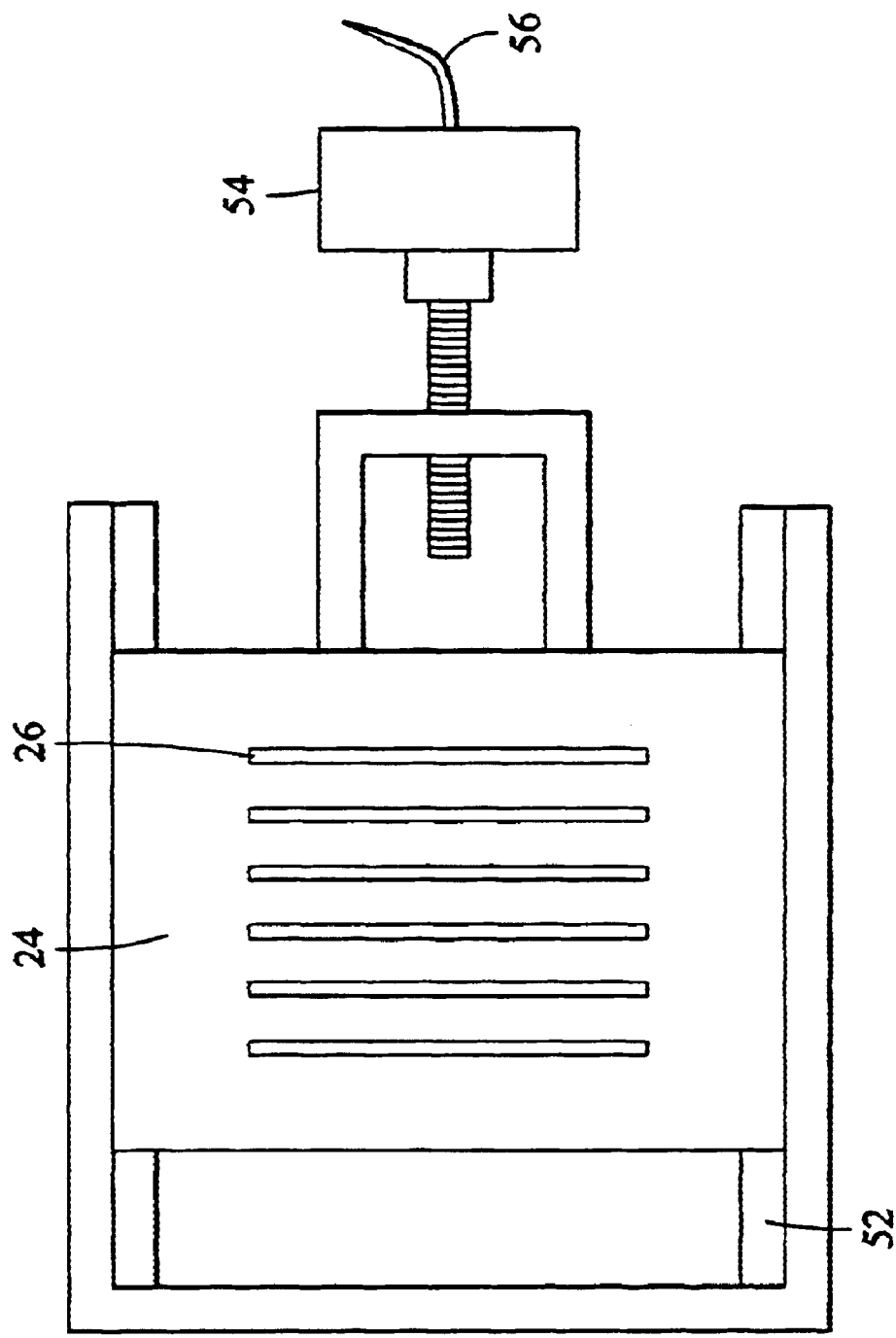
FIG. 5 is a schematic diagram of a movable mask constructed according to an alternate embodiment of the invention.

It is also possible to "scan" the whole CCD light sensitive area with a "movable" mask with slits. FIG. 5 shows a movable mask 24 sits on a track 52 and is connected to a step motor 54, which is connected to the computer 10 through cable 56. If the mask 24 has 20 slits, all of the CCD pixels (400 rows) can be "scanned", by moving the mask in nineteen steps.

Figure 6:
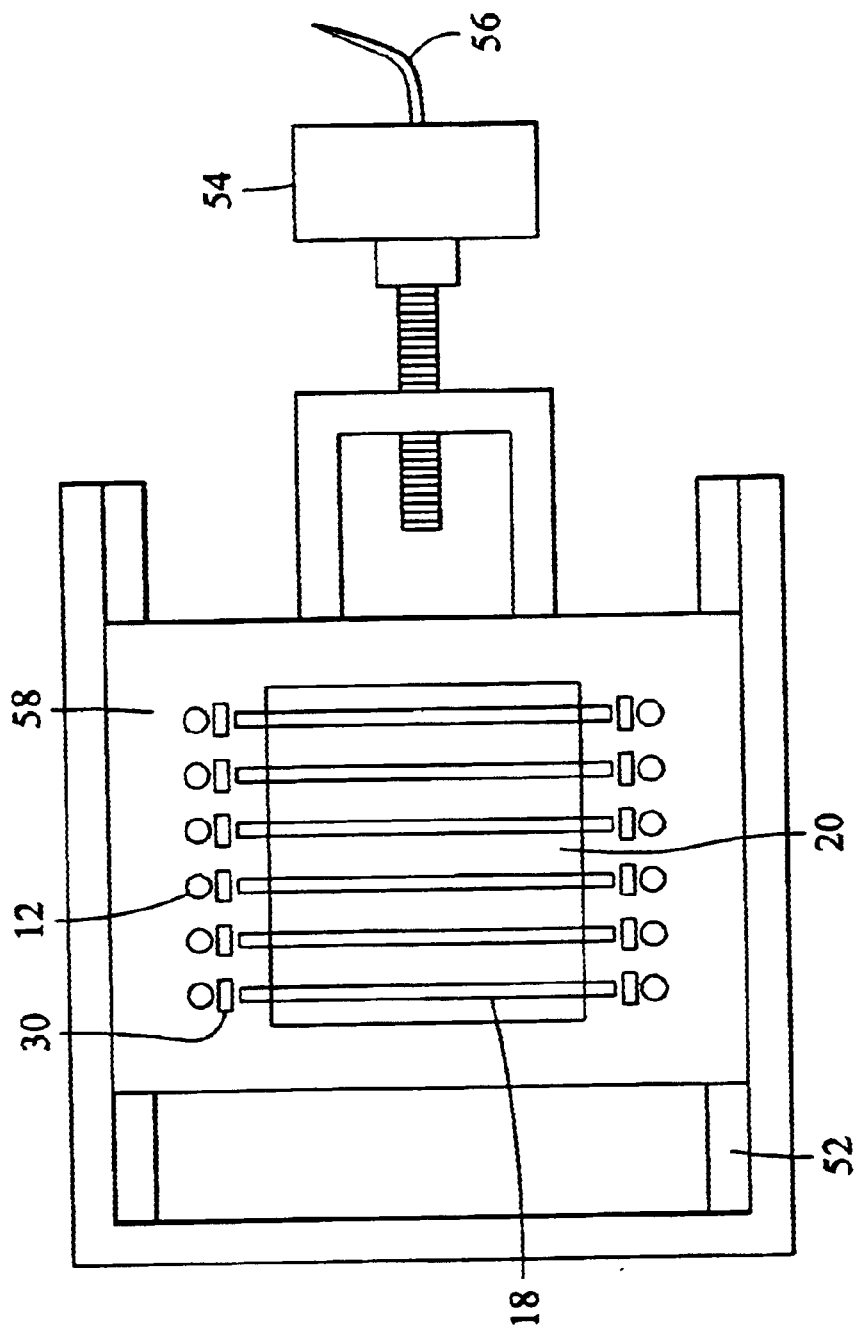
FIG. 6 is a schematic diagram of a movable sample implementing another feature of the invention.

There is another scanning method to achieve the time resolved spectroscopy of the whole sample area. FIG. 6 shows a sample sitting on a movable transparent plate 58 that is connected to a step motor 54 connected to the computer 10 through cable 56. With the movable sample, there is no need to have the whole area of the sample 20 illuminated. One may use a linear light source 18, which is fixed in space, to illuminate only the area that will have the image formed on the slits of the CCD. In the example demonstrated above, the whole sample area can be "scanned", by moving the sample in nineteen steps.

In the example described above, the CCD is a three-phase CCD. However, any other types of CCD can be used for the described time resolved fluorescence study without using a gated detector. The mask 24 can also be a pattern painted on the CCD surface.

Figure 7A:
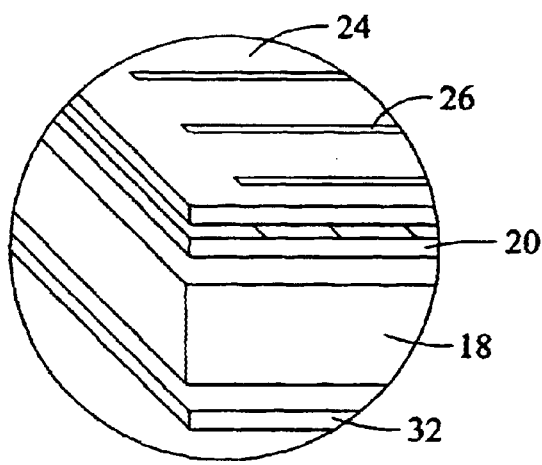
FIGS. 7 and 7A are schematic diagrams of a second embodiment of the time-resolved fluorescence detection system without a gating device, where the mask is placed on top of the sample.
Figure 7:
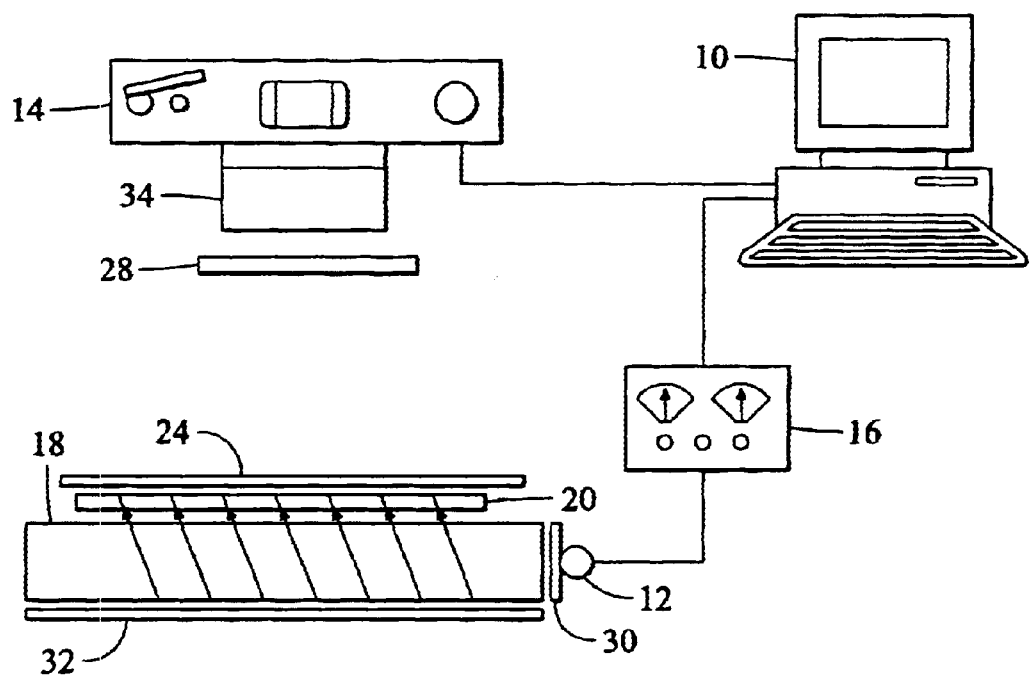

In the embodiment described, the mask 24 is placed right on top of the CCD 22, which is the "image plane". In theory, the mask can also be located on the "object plane", or on top of the object 20, which is the gel. Place the mask on the image plane, however, is preferable, because the masked area has a minimum light exposure. With the mask in the object plane, leakage light as well as distortion in the image, which occurs in almost all image systems, may contribute to a background noise. A diagram showing the mask at the object plane is given in FIGS. 7 and 7A.

While only a limited number of embodiments have been shown and described herein, modifications may be made within the scope of the present invention. This invention can also be applied to study time dependent light emission caused by excitation with a electric pulse, such as electric caused light emission in a solid, and electric discharge caused light emission in gas.

The invention claimed is:

1. An apparatus for detecting time-resolved fluorescence of a material, comprising:
   a pulsed light source;
   a charge coupled device (CCD) with rows and columns of light sensitive pixels;
   a material interposed between the pulsed light source and the CCD, said material having a decaying fluorescence property to be measured responsive to exposure to the pulsed light source;
   a mask with at least a light-transmission aperture interposed between the material and the CCD, said mask exposing less than 50% of light sensitive pixels of the CCD and said aperture exposing at least a selected pixel on the CCD; and
   means for transferring charge in the CCD from the selected pixel to another pixel with a known temporal relationship between the light pulse emitted by the pulsed light source and the charge transfer.

2. The apparatus of claim 1 wherein said aperture is a slit.

3. The apparatus of claim 1 further comprising means for expanding the light beam from a point like light source to a linear light source, or a plane light source.

4. The apparatus of claim 1 wherein said mask is painted on the CCD.

5. The apparatus of claim 1 wherein said mask is movable relative to the CCD.

6. The apparatus of claim 1 further comprising means for moving the material relative to the light source.

7. The apparatus of claim 6 wherein the means for moving the material includes a movable material holder on which the material is placed.

8. The apparatus of claim 1 further comprising a color filter interposed between the light source and the material.

9. The apparatus of claim 1 further comprising a lens to collect the fluorescent light from the material.

10. The apparatus of claim 1 wherein the means for transferring the charge in the CCD is an electronic device.

11. The apparatus of claim 10 further comprising a computer to trigger the light source, to trigger the electronic device and to collect data.

12. The apparatus of claim 1 wherein said mask is a programmable mask with the location and shape of the light-transmission aperture programmed electronically.

13. The apparatus of claim 12 wherein said programmable mask is a LCD panel.

14. The apparatus of claim 1 wherein said mask is placed proximate said CCD.

15. The apparatus of claim 1 wherein said mask is placed proximate said material.

16. A method for time-resolved light emission study of a material, comprising:
   pulse exciting the material to emit fluorescent light;
   detecting the fluorescent light with rows and columns of light sensitive pixels where electric charge can be stored;
   exposing less than 50% of the light sensitive pixels to the fluorescent light; and
   transferring charge stored in the exposed light sensitive pixels to unexposed pixels with a known temporal relationship between the light pulse emitted by the pulsed light source and the charge transfer.

17. The method of claim 16 wherein the step of pulse exciting the material includes using a device selected from the group consisting of a pulsed laser, a flash lamp, a LED, or an electric pulse.

18. The method of claim 16 further comprising the step of expanding the light beam from a point like light source to a linear light source, or a plane light source.

19. The method of claim 16 where the step of detecting the fluorescent light includes using a charge coupled device (CCD).

20. The method of claim 16 where in the step of exposing less than 50% of the said light sensitive pixels includes using a mask having an aperture.

21. The method of claim 20 wherein said mask is a layer of light blocking material painted on the light sensitive pixels.

22. The method of claim 20, further including the step of providing a programmable mask adapted to program the location and shape of the aperture.

23. The method of claim 22 said programmable mask is a LCD panel.

24. The method of claim 20 wherein said mask is placed proximate said CCD.

25. The method of claim 20 wherein said mask is placed proximate said material.

26. The method of claim 16, further including the step of changing the location of the material to be observed relative to the rows and columns of pixels.

27. The method according to claim 26 wherein the step of changing the location of the material includes moving the mask.

28. The method according to claim 27 wherein the step of moving the location of the mask includes using a motor.

29. The method according to claim 26 wherein the step of changing the location of the material includes the step of moving the material.

30. The method according to claim 29 wherein the step of changing the location of the materials includes the step of using a motor.

31. The method of claim 16 where said step of transferring charge includes the step of using an electronic device which generate electric signal of a predetermined wave form and amplitude.

32. The method of claim 16 further including the step of filtering the pulse exciting the material.

33. The method of claim 16 further comprising the step of collecting the fluorescent light from the said material using a lens.

34. The method of claim 16 further comprising the step of using a computer to trigger the light source, to trigger the said electronic device and to collect data.

* * * * *

UNITED STATES PATENT AND TRADEMARK OFFICE
CERTIFICATE OF CORRECTION

PATENT NO.    : 6,740,890 B1
DATED         : May 25, 2004
INVENTOR(S)   : Tai et al.

It is certified that error appears in the above-identified patent and that said Letters Patent is hereby corrected as shown below:

Title page,
Item [12], "Tai" should read -- Tai et al. --
Item [76], Inventor, should add -- Ping-Kaung Tai, Holland, OH (US) --.

Column 3,
Line 25, "CC!) camera" should read -- CCD camera --.

Column 4,
Line 52, "over 10,0 $\mu$s), the" should read -- over 10.0$\mu$s), the --.

Column 5,
Line 8, "row n + 1 will" should read -- row n + 11 will --.
Line 11, "row n + 1, therefore," should read -- row n + 11, therefore, --.
Line 13, "of 10.0 $\mu$s." should read -- of 100.0$\mu$s. --.
Line 26, "CCD 22. In" should read -- CCD 22. ¶ In --.
Line 48, "to n + 1 and" should read -- to n + 11 and --.

Column 8,
Line 25, "claim 22 said" should read -- claim 22 wherein said --.

Signed and Sealed this

Fourth Day of January, 2005

JON W. DUDAS
*Director of the United States Patent and Trademark Office*